US00PP26298P3

(12) United States Plant Patent
Meilland

(10) Patent No.: US PP26,298 P3
(45) Date of Patent: Jan. 12, 2016

(54) FLORIBUNDA ROSE PLANT NAMED 'MEIPEPORIA'

(50) Latin Name: *Rosa hybrida*
Varietal Denomination: Meipeporia

(71) Applicant: CP DELAWARE, INC., Wilmington, DE (US)

(72) Inventor: Alain A. Meilland, Antibes (FR)

(73) Assignee: CP DELAWARE, INC., Wilmington, DE (US)

( * ) Notice: Subject to any disclaimer, the term of this patent is extended or adjusted under 35 U.S.C. 154(b) by 175 days.

(21) Appl. No.: 13/998,767

(22) Filed: Dec. 4, 2013

(65) Prior Publication Data

US 2015/0156934 P1 Jun. 4, 2015

(51) Int. Cl.
*A01H 5/02* (2006.01)

(52) U.S. Cl.
USPC ..... Plt./151

(58) Field of Classification Search
USPC ..... Plt./101, 141, 151
See application file for complete search history.

*Primary Examiner* — Susan McCormick Ewoldt
(74) *Attorney, Agent, or Firm* — Buchanan, Ingersoll & Rooney PC

(57) ABSTRACT

A new and distinct Floribunda rose plant is provided that commonly commences blooming medium in the season and forms abundantly and substantially continuously attractive dark red double blossoms with a particularly impressive blooming propensity in the autumn. The growth habit is bushy and strong vegetation is formed. The vegetation is very dense dark green and bears a matte finish on the upper surface. The disease tolerance is very good particularly with respect to *Botrytis*. The plant is particularly well suited for providing attractive ornamentation in parks and gardens.

1 Drawing Sheet

Figures 1, 2, 3, 4, 5, 6, 7, 8, 9, 10, 11, 12, 13, 14, 15, 16:
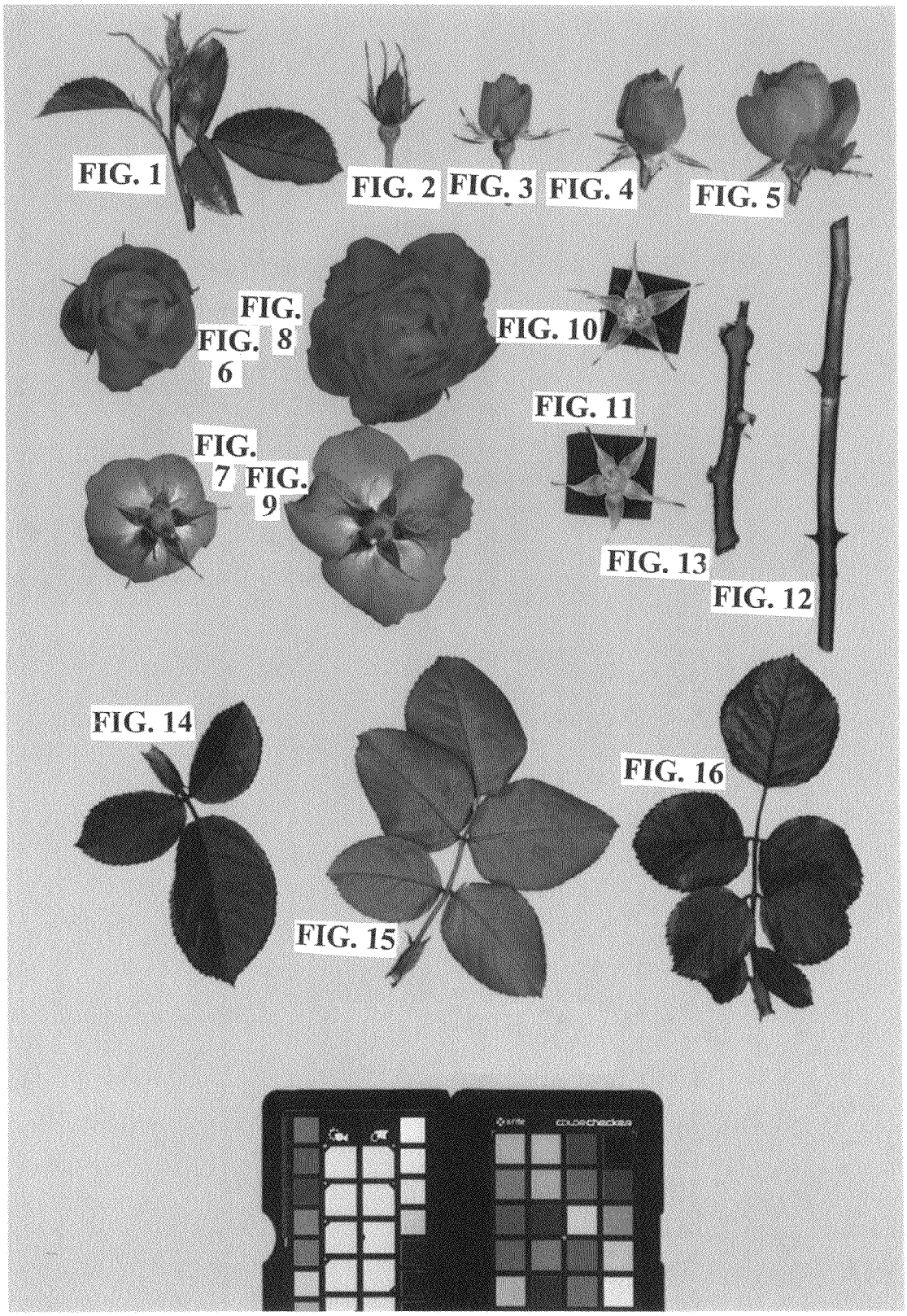

Botanical/commercial classification: *Rosa hybrida*/Floribunda Rose Plant.

Varietal denomination: cv. Meipeporia.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was the product of the cross of the 'Meinoiral' variety (non-patented in the United States) and 'Kortikel' variety (non-patented in the United States). The male parent (i.e., the pollen parent) was the 'Radrazz' variety (U.S. Plant Pat. No. 11,836). The 'Kortikel' variety is marketed under the GOLDEN HOLSTEIN trademark and the 'Radrazz' variety is marketed under the KNOCK OUT trademark.

The parentage of the new variety can be summarized as follows:

('Meinoiral'×'Kortikel')×'Radrazz'.

The seeds resulting from the above pollination were sown and small plants were obtained which were physically and biologically different from each other. Selective study resulted in the identification of a single plant of the new variety.

It was found that the new Floribunda rose plant of the present invention:

(a) displays a bushy growth habit with strong vegetation,
(b) forms in abundance on a substantially continuous basis attractive dark red double blossoms commonly with a particularly impressive blooming propensity in the autumn, (c) exhibits very dense dark green foliage with a matte finish on the upper surface,
(d) exhibits very good tolerance to disease, particularly with respect to *Botrytis*, and
(e) is well suited for providing attractive ornamentation in parks and gardens.

The blooming tends to commence medium in the season, during observations to date.

The new variety well meets the needs of the horticultural industry and can be grown to advantage where attractive ornamentation is to be provided.

The new variety can be readily distinguished from its ancestors. For instance, the 'Meinoiral' variety forms dissimilar blossoms having a medium pink coloration. The 'Kortikel' variety forms dissimilar blossoms having a yellow coloration. The 'Radrazz' variety forms dissimilar red blossoms having a substantially lesser number of petals (e.g., approximately 10 petals).

The new variety also can be readily distinguished from the 'Meigekanu' variety (U.S. Plant Pat. No. 6,384, granted Nov. 8, 1988) and the 'Radral' variety (U.S. Plant Pat. No. 19,803, granted Mar. 10, 2009) upon an inspection of the blossoms. More specifically, the 'Meigekanu' variety forms dissimilar semi-double bright red blossoms and the 'Radral' forms orange blossoms that finish to a coral-salmon coloration.

The new variety has been found to undergo asexual propagation in France by a number of routes, including budding, grafting, and the use of cuttings. Asexual propagation by the above-mentioned techniques at Le Cannet des Maures, Var, France, has shown that the characteristics of the new variety are stable and are strictly transmissible by such asexual propagation from one generation to another. Accordingly, the new variety undergoes asexual propagation in a true-to-type manner.

The new variety has been named 'Meipeporia'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately 1½ years of age and were observed during July while growing outdoors on their own roots at Le Cannet des Maures, Var, France. Standard comparative color information is included at the bottom of the photograph.

FIG. 1—illustrates a specimen of a young shoot;

FIG. 2—illustrates a specimen of a floral bud at the initial opening of the sepals;

FIG. 3—illustrates a specimen of a floral bud wherein the sepals are more fully open;

FIG. 4—illustrates a specimen of a floral bud at the opening of the petals;

FIG. 5—illustrates a specimen of a flower in the course of further opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED BOTANICAL DESCRIPTION

The chart used in the identification of the colors is that of The Royal Horticultural Society (R.H.S. Colour Chart—1995). The description is based on the observation of 1½-year-old plants during May while growing outdoors on their own roots at Le Cannet des Maures, Var, France.

Class: Floribunda.

Plant:

*Growth habit*.—Bushy.

*Height*.—Approximately 50 cm on average.

*Width*.—Approximately 50 cm on average.

Branches:

*Color*.—Young stems: near Yellow-Green Group 146C and 146D. Adult wood: near Yellow-Green Group 146B.

*Thorns*.—On young stems: Configuration: with an oval base. Quantity: approximately 1 on average on a stem length of 10 cm. Length: approximately 4 mm on average. Color: near Yellow-Green Group 148D. On adult stems: Configuration: upright on the upper surface and slightly concave on the under surface with an oval base. Quantity: approximately 1 on average over a stem length of 10 cm. Length: approximately 7 mm on average. Color: near Greyed-Orange Group 174A.

Leaves:

*Stipules*.—Adnate, pectinate, rather broad, approximately 2 cm in length on average, approximately 1.1 cm in width on average, near Green Group 138B on the upper surface, and near Green Group 138A on the under surface.

*Petioles*.—Upper surface: near Green Group 138B in coloration. Under surface: near Yellow-Green Group 145A in coloration. Texture: non-glandular on the upper surface, and without small prickles on the under surface.

*Rachis*.—Upper surface: near Green Group 137C in coloration. Under surface: near Yellow-Green Group 138A in coloration.

*Length*.—Commonly approximately 13.5 cm for a seven-leaflet leaf.

*Width*.—Commonly approximately 9.5 cm for a seven-leaflet leaf.

*Leaflets*.—Number: 3, 5 and 7 (most often). Shape: generally oval with an acuminate tip and a rounded base. Size: the terminal leaflets commonly are approximately 7.5 cm in length on average and approximately 5.1 cm in width on average. Serration: slightly denticulate, small and single. Texture: physically firm and leathery. Color (young foliage): Upper surface: near Green Group 137A. Under surface: near Yellow-Green Group 148A. Color (adult foliage): Upper surface: near Green Group 137A. Under surface: near Green Group 138A. Venation: alternate pinnate, and near Greyed-Yellow Group 160B in coloration.

Inflorescence:

*Number of flowers*.—Commonly approximately 1 to 5 blossoms per stem.

*Peduncle*.—Glandular, approximately 3 to 4 cm in length on average, approximately 2 mm in diameter on average, and near Yellow-Green Group 146C in coloration.

*Sepals*.—Upper surface: tomentose and near Yellow-Green Group 147C in coloration. Under surface: smooth and near Yellow-Green Group 146B in coloration. Shape: longish and narrow with a substantially rounded base. Size: approximately 2.7 cm in length on average, and approximately 5 mm in width at the widest point on average.

*Buds*.—Shape: substantially conical. Size: medium. Length: approximately 1.5 cm on average. Width: approximately 1.4 cm at the widest point on average. Color as calyx breaks: Upper surface: near Red Group 47A and 47B. Under surface: near Red Group 54A and 54B amply suffused with near Red Group 50A.

*Flower*.—Shape: cup-shaped. Diameter: approximately 8 cm on average. Depth: approximately 4 cm on average. Color (in the course of opening): Upper surface: near Red Group 47A and 47B. Under surface: near Red Group 54A and 54B amply suffused with near Red Group 50A. Color (open flower): Upper surface: near Red-Purple Group 57B and 57C amply suffused with Red Group 50A. Under surface: near Red-Purple Group 57D amply suffused with near Red Group 50B and Red-Purple Group 57B. Fragrance: none detected. Petal number: approximately 25 on average under normal growing conditions. Petal shape: with a substantially rounded tip and an obtuse base. Petal texture: leathery and somewhat firm. Petal length: approximately 3.8 cm on average. Petal width:

approximately 3.5 cm on average. Petal arrangement: imbricated, and without petaloids. Petal drop: good with the petals commonly detaching cleanly before drying. Stamen number: approximately 69 on average. Anthers: regularly arranged around the styles, approximately 2 mm in size on average, and near Yellow-Orange Group 21B in coloration. Filaments: approximately 3 mm in length on average, and near Yellow-White Group 158B in coloration. Pollen: not available for observation. Pistils: approximately 71 on average. Stigmas: approximately 1 mm in size on average, and near Yellow Group 2C in coloration. Styles: approximately 4 mm in length on average, and near Yellow Group 150D in coloration. Receptacle: smooth, pitcher-shaped in longitudinal section, approximately 1.1 cm in length on average, approximately 8 mm in width on average at the widest point, and near Yellow-Green Group 146B in coloration.

Development:

*Vegetation*.—Strong.

*Blooming*.—Medium season, very abundant and substantially continuous.

*Tolerance to disease*.—Very good, particularly with respect to *Botrytis*.

The new 'Meipeporia' variety has not been observed under all possible environmental conditions to date. Accordingly, it is possible that the phenotypic expression may vary somewhat with changes in light intensity and duration, cultural practices, and other environmental conditions.

I claim:

1. A new and distinct Floribunda rose plant characterized by the following characteristics:

(a) displays a bushy growth habit with strong vegetation, (b) forms in abundance on a substantially continuous basis attractive dark red double blossoms commonly with a particularly impressive blooming propensity in the autumn, (c) exhibits very dense dark green foliage with a matte finish on the upper surface, (d) exhibits very good tolerance to disease, particularly with respect to *Botrytis*, and (e) is well suited for providing attractive ornamentation in parks and gardens;

substantially as shown and described.

* * * * *